US010576073B2

(12) United States Patent
Patterson et al.

(10) Patent No.: US 10,576,073 B2
(45) Date of Patent: *Mar. 3, 2020

(54) CRYSTALLINE FORM OF A 4-[2-(2-FLUORO-PHENOXYMETHYL)PHENYL]PIPERIDINE COMPOUND

(71) Applicant: THERAVANCE BIOPHARMA R&D IP, LLC, South San Francisco, CA (US)

(72) Inventors: Lori Jean Patterson, San Francisco, CA (US); Robert S. Chao, Santa Clara, CA (US); Miroslav Rapta, San Carlos, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/244,956

(22) Filed: Jan. 10, 2019

(65) Prior Publication Data

US 2019/0142816 A1 May 16, 2019

Related U.S. Application Data

(60) Continuation of application No. 15/586,531, filed on May 4, 2017, now Pat. No. 10,226,454, which is a continuation of application No. 14/728,079, filed on Jun. 2, 2015, now abandoned, which is a division of application No. 14/060,846, filed on Oct. 23, 2013, now Pat. No. 9,073,859, which is a division of application No. 13/632,588, filed on Oct. 1, 2012, now Pat. No. 8,592,596, which is a division of application No. 12/617,838, filed on Nov. 13, 2009, now Pat. No. 8,304,433.

(60) Provisional application No. 61/114,541, filed on Nov. 14, 2008.

(51) Int. Cl.
*A61K 31/4465* (2006.01)
*C07D 211/22* (2006.01)
*C07D 211/32* (2006.01)

(52) U.S. Cl.
CPC ........ *A61K 31/4465* (2013.01); *C07D 211/22* (2013.01); *C07D 211/32* (2013.01)

(58) Field of Classification Search
CPC .................................................. A61K 31/4465
USPC ........................................................ 514/317
See application file for complete search history.

(56) References Cited

U.S. PATENT DOCUMENTS

| 4,007,196 A | 2/1977 | Christensen et al. |
| 4,198,417 A | 4/1980 | Ong et al. |
| 4,229,449 A | 10/1980 | Melloni et al. |
| 4,241,071 A | 12/1980 | Martin et al. |
| 4,243,807 A | 1/1981 | Friebe et al. |
| 5,023,269 A | 6/1991 | Robertson et al. |
| 5,037,841 A | 8/1991 | Schohe et al. |
| 5,614,518 A | 3/1997 | Leeson et al. |
| 6,518,284 B2 | 2/2003 | Venero et al. |
| 6,630,504 B2 | 10/2003 | Andrews et al. |
| 7,138,407 B2 | 11/2006 | Ruhland et al. |
| 7,294,637 B2 | 11/2007 | Aquila et al. |
| 7,378,436 B2 | 5/2008 | Fish et al. |
| 7,384,941 B2 | 6/2008 | Walter et al. |
| 7,888,386 B2 | 2/2011 | Stangeland et al. |
| 8,247,433 B2 | 8/2012 | Stangeland et al. |
| 8,304,432 B2 | 11/2012 | Patterson et al. |
| 8,304,433 B2 | 11/2012 | Patterson et al. |
| 8,592,596 B2 | 11/2013 | Patterson et al. |
| 8,604,058 B2 | 12/2013 | Patterson et al. |
| 9,073,859 B2 | 7/2015 | Patterson et al. |
| 9,162,982 B2 | 10/2015 | Patterson et al. |
| 9,675,599 B2 | 6/2017 | Patterson et al. |
| 10,034,870 B2 | 7/2018 | Patterson et al. |
| 2005/0245519 A1 | 11/2005 | Barta et al. |
| 2006/0293360 A1 | 12/2006 | Bang-Andersen et al. |
| 2007/0072859 A1 | 3/2007 | Boulet et al. |
| 2007/0105870 A1 | 5/2007 | Bish et al. |
| 2007/0142389 A1 | 6/2007 | Bruendl et al. |
| 2009/0018132 A1 | 1/2009 | Degnan et al. |
| 2016/0022660 A1 | 1/2016 | Patterson et al. |
| 2019/0134019 A1 | 5/2019 | Patterson et al. |

FOREIGN PATENT DOCUMENTS

| EP | 0190496 A2 | 8/1985 |
| EP | 1670760 | 6/2006 |
| WO | 2004/087155 A1 | 10/2004 |
| WO | 2006/097766 A1 | 9/2006 |
| WO | 2008/023258 A1 | 2/2008 |
| WO | 2009/081259 A1 | 7/2009 |

OTHER PUBLICATIONS

Bergel et al., "Synthetic Analgesics. Part I. Synthesis of Basic Benzofuran Derivatives and Certain 4-Phenylpiperidine Compounds", Journal of the Chemical Society, pp. 261-265 (1944).
Cheronis, "Purification of solids by crystallization", Semimicro expe. Org. Chem., p. 31-43 (1958).
PCT Notification of Transmittal of the International Search Report and the Written Opinion of the International Searching Authority, or the Declaration of PCT/US2009/064306 dated Feb. 24, 2010.
Gray et al., "Discovery and Pharmacological Characterization of Aryl Piperazine- and Piperidine Ethers as Dual Acting Norepinephrine Reuptake Inhibitors and 5-HT1A Partial Agonists", BioOrganic & Medicinal Chemistry Letters doi 10.1016/j.bmcl.2009.10.014(2009).
Lee et al., "A review of SSRIs . . . ", Exp. Opin. Pharmcother. v.11(7) p. 2813-2825 (2010).
Liu et al., "Unbound brain . . . ", Am. Soc. Pharm. Exp. Ther. v.37(7) p. 1548-1556 (2009).
Net, Wikipedia, p. 1-9 (2014).

(Continued)

*Primary Examiner* — Taofiq A Solola
(74) *Attorney, Agent, or Firm* — Jeffrey A. Hagenah

(57) ABSTRACT

The invention provides a crystalline hydrochloride salt of 4-[2-(2,4,6-trifluorophenoxymethyl)phenyl]piperidine. This invention also provides pharmaceutical compositions comprising the crystalline salt, processes and intermediates for preparing the crystalline salt, and methods of using the crystalline salt to treat diseases.

11 Claims, 4 Drawing Sheets

(56) References Cited

OTHER PUBLICATIONS

SNRIs, Wikipedia, p. 1-18 (2014).
SSRI, Wikipedia, p. 1-6 (2014).
St. John's Wort, Medline Plus, p. 1-8 (2014).
Who, "Classification of mental and behavioral disorders", p. 1-268 (1993).
Arai, "Parinsonism assoc . . . " J. Neurosurg. Psychiatry, v. 74, pp. 134-139 (2003).
Antiparkinson Medication, Wikipedia, pp. 1-4 (2016).
Antiparkinson Medication, Wikipedia, pp. 1-4 (2017).
Antiparkinson Drugs, Medical Dictionary, pp. 1-4 (2017).
Drug Interaction Report, Selegiline and Milnacipran, pp. 1-3 (2017).
Selegiline, Wikipedia, pp. 1-6 (2017).
Caira, Crystalline Polymorphism of Organic Compounds, Topics in Current Chemistry, 1998, vol. 198, pp. 164-208, Springer Verlag Berlin Heidelberg.
Stahl, Handbook of Pharmaceutical Salts, Properties, Selection, and Use, 2002, pp. 258-261, Verlag Helvetica Chimica Acta, Zurich.
Guillory, Generation of Polymorphs, Hydrates, Solvates, and Amorphous Solids, Polymorphism in Pharmaceutical Solids, 1999, pp. 183-226, Edited by Brittain, Marcel Dekker, Inc., New York.
Non-Final Office Action for U.S. Appl. No. 15/591,419, dated Jan. 10, 2018.
Preliminary Amendment for U.S. Appl. No. 15/591,419, filed Nov. 10, 2017.
Response for U.S. Appl. No. 15/591,419, filed Mar. 2, 2018.

CRYSTALLINE FORM OF A 4-[2-(2-FLUOROPHENOXYMETHYL)PH-ENYL]PIPERIDINE COMPOUND

CROSS-REFERENCE TO RELATED APPLICATIONS

This application is a continuation of U.S. application Ser. No. 15/586,531, filed on May 4, 2017; which application is a continuation of U.S. application Ser. No. 14/728,079, filed on Jun. 2, 2015 (now abandoned); which application is a divisional of U.S. application Ser. No. 14/060,846, filed Oct. 23, 2013 (now U.S. Pat. No. 9,073,859 B2); which application is a divisional of U.S. application Ser. No. 13/632,588, filed Oct. 1, 2012 (now U.S. Pat. No. 8,592,596 B2); which application is a divisional of U.S application Ser. No. 12/617,838, filed Nov. 13, 2009 (now U.S. Pat. No. 8,304,433 B2); which application claims the benefit of U.S. Provisional Application No. 61/114,541, filed on Nov. 14, 2008; the entire disclosures of which are incorporated herein by reference in their entirety.

BACKGROUND OF THE INVENTION

Field of the Invention

The present invention relates to a novel crystalline form of a 4-[2-(2-fluorophenoxymethyl)phenyl]piperidine compound, which has activity as a serotonin (5-HT) and norepinephrine (NE) reuptake inhibitor. This invention also relates to pharmaceutical compositions comprising the crystalline compound or prepared from such compound, processes and intermediates for preparing the crystalline compound, and methods of using such compound to treat a pain disorder, such as neuropathic pain, and other ailments.

STATE OF THE ART

Pain is an unpleasant sensory and emotional experience associated with actual or potential tissue damage, or described in terms of such damage (International Association for the Study of Pain (IASP), Pain Terminology). Chronic pain persists beyond acute pain or beyond the expected time for an injury to heal (American Pain Society. "Pain Control in the Primary Care Setting." 2006:15). Neuropathic pain is pain initiated or caused by a primary lesion or dysfunction in the nervous system. Peripheral neuropathic pain occurs when the lesion or dysfunction affects the peripheral nervous system and central neuropathic pain when the lesion or dysfunction affects the central nervous system (IASP).

Several types of therapeutic agents are currently used to treat neuropathic pain including, for example, tricyclic antidepressants, serotonin and norepinephrine reuptake inhibitors, calcium channel ligands (e.g., gabapentin and pregabalin), topical lidocaine, and opioid agonists (e.g., morphine, oxycodone, methadone, levorphanol and tramadol).

4-[2-(2,4,6-Trifluorophenoxymethyl)phenyl]piperidine, described herein, inhibits the reuptake of both serotonin and norepinephrine by binding to the serotonin and norepinephrine transporters. When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point (i.e. greater than about 150° C.), which allows the material to be processed, for example, micronized, without significant decomposition.

Accordingly, a need exists for a stable, non-deliquescent form of 4-[2-(2,4,6-trifluorophenoxymethyl)phenyl]piperidine which has an acceptable level of hygroscopicity and a relatively high melting point.

SUMMARY OF THE INVENTION

The present invention relates to a crystalline hydrochloride salt of 4-[2-(2,4,6-trifluorophenoxymethyl)phenyl]piperidine.

One aspect of the invention relates to processes for preparing a crystalline hydrochloride salt of 4-[2-(2,4,6-trifluorophenoxymethyl)phenyl]piperidine. In one embodiment, a process for preparing a crystalline hydrochloride salt of 4-[2-(2,4,6-trifluorophenoxymethyl)phenyl]piperidine comprises the steps of: a) treating a hydrochloride salt of 4-[2-(2,4,6-trifluorophenoxymethyl)phenyl]piperidine with ethyl acetate and ethanol to complete dissolution; b) cooling to effect crystallization; c) isolating the resulting solids to yield the crystalline hydrochloride salt of the invention. In another embodiment, this crystalline hydrochloride salt is further d) treated with isopropanol and water to complete dissolution; e) cooled to effect crystallization; and f) the resulting solids isolated to yield the crystalline hydrochloride salt of the invention.

Another aspect of the invention relates to a process for purifying 4-[2-(2,4,6-trifluorophenoxymethyl)phenyl]piperidine. In one embodiment, this process comprises forming a crystalline hydrochloride salt of 4-[2-(2,4,6-trifluorophenoxymethyl)phenyl]piperidine. The invention also relates to products prepared by the processes described herein.

One aspect of the invention relates to a pharmaceutical composition comprising a pharmaceutically acceptable carrier and a crystalline hydrochloride salt of 4-[2-(2,4,6-trifluorophenoxymethyl)phenyl]piperidine. Such compositions may optionally contain other active agents such as anti-Alzheimer's agents, anticonvulsants, antidepressants, anti-Parkinson's agents, dual serotonin-norepinephrine reuptake inhibitors, non-steroidal anti-inflammatory agents, norepinephrine reuptake inhibitors, opioid agonists, opioid antagonists, selective serotonin reuptake inhibitors, sodium channel blockers, sympatholytics, and combinations thereof. Accordingly, in yet another aspect of the invention, a pharmaceutical composition comprises the crystalline salt of the invention, a second active agent, and a pharmaceutically acceptable carrier. Another aspect of the invention relates to a combination of active agents, comprising the crystalline salt of the invention and a second active agent. The crystalline salt of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising the crystalline salt of the invention and a first pharmaceutically acceptable carrier; and a second pharmaceutical composition comprising a second active agent and a second pharmaceutically acceptable carrier. The invention also relates to a kit containing such pharmaceutical compositions, for example where the first and second pharmaceutical compositions are separate pharmaceutical compositions.

4-[2-(2,4,6-Trifluorophenoxymethyl)phenyl]piperidine possesses serotonin reuptake inhibitory activity and norepinephrine reuptake inhibitory activity. The crystalline hydrochloride salt of this compound is expected to have the same activity and thus the same utility as a therapeutic agent for treating patients suffering from a disease or disorder that is treated by the inhibition of the serotonin and/or the norepinephrine transporter. Thus, one aspect of the invention relates to a method of treating: a pain disorder such as neuropathic pain or fibromyalgia; a depressive disorder such as major depression; an affective disorder such as an anxiety disorder; attention deficit hyperactivity disorder; a cognitive disorder such as dementia; stress urinary incontinence; chronic fatigue syndrome; obesity; or vasomotor symptoms associated with menopause, comprising administering to a patient a therapeutically effective amount of the crystalline compound of the invention.

Yet another aspect of the invention relates to the use of the crystalline compound of the invention for the manufacture of medicaments, especially for the manufacture of medicaments useful for treating pain disorders, depressive disorders, affective disorders, attention deficit hyperactivity disorder, cognitive disorders, stress urinary incontinence, for inhibiting serotonin reuptake in a mammal, or for inhibiting norepinephrine reuptake in a mammal. Other aspects and embodiments of the invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
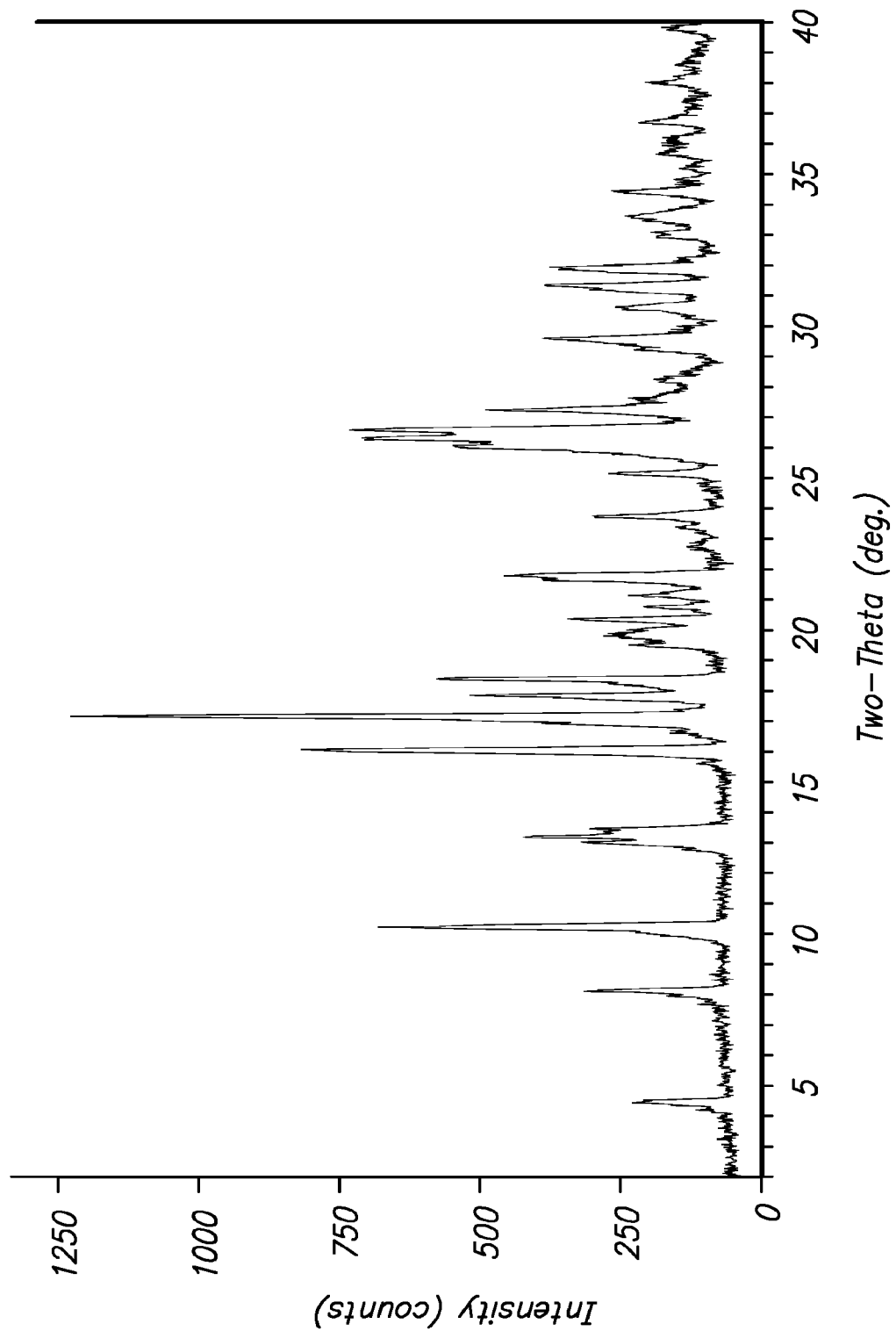
FIG. 1 shows a powder x-ray diffraction (PXRD) pattern of the crystalline hydrochloride salt of 4-[2-(2,4,6-trifluorophenoxymethyl)phenyl]piperidine.

This invention provides a crystalline hydrochloride salt of 4-[2-(2,4,6-trifluorophenoxymethyl)phenyl]piperidine. Surprisingly, this crystalline compound has been found not to be deliquescent, even when exposed to atmospheric moisture. Additionally, this crystalline compound has an acceptable level of hygroscopicity and a high melting point.

The single crystal of the drug molecule exhibits a monoclinic symmetry ($P2_1C$ space group), with the following unit-cell parameters: A=C=90°, B=104.595°; a=11.631 Å, b=7.057 Å, c=42.532 Å. While not wishing to be limited by theory, based upon the X-ray crystallographic data, the crystal is believed to be built around the water molecule and the water content was determined from the water occupancy factor in the unit cell using the thermal motion parameters of the atoms and overall observed structure factors.

Thus, in one embodiment, the crystalline hydrochloride salt of 4-[2-(2,4,6-trifluorophenoxymethyl)phenyl]piperidine may contain a certain amount of water that is absorbed on the surface of the crystalline material or forms part of the crystalline structure.

In one particular embodiment, the crystalline hydrochloride salt may contain an amount of water ranging from about 0.2 wt % to about 0.8 wt % that is absorbed on the crystal surface; and in another embodiment from about 0.4 wt % to about 0.6 wt %.

In yet another particular embodiment, the crystalline hydrochloride salt may contain from about 0.25 to about 0.50 moles of water that form part of the crystalline structure; and in another embodiment from about 0.30 to about 0.40 moles. In one exemplary embodiment, there are about 0.32 moles of water present for every one mole of the 4-[2-(2,4,6-trifluorophenoxymethyl)phenyl]piperidine hydrochloride salt.

DEFINITIONS

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

As used herein, the phrase "of the formula", "having the formula" or "having the structure" is not intended to be limiting and is used in the same way that the term "comprising" is commonly used.

The term "melting point" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The term "therapeutically effective amount" means an amount sufficient to effect treatment when administered to a patient in need thereof, i.e., the amount of drug needed to obtain the desired therapeutic effect. For example, a therapeutically effective amount for treating neuropathic pain is an amount of compound needed to, for example, reduce, suppress, eliminate or prevent the symptoms of neuropathic pain or to treat the underlying cause of neuropathic pain. On the other hand, the term "effective amount" means an amount sufficient to obtain a desired result, which may not necessary be a therapeutic result. For example, when studying a system comprising a norepinephrine transporter, an "effective amount" may be the amount needed to inhibit norepinephrine reuptake.

The term "treating" or "treatment" as used herein means the treating or treatment of a disease or medical condition (such as neuropathic pain) in a patient, such as a mammal (particularly a human), that includes one or more of the following: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating neuropathic pain" would include preventing neuropathic pain from occurring, ameliorating neuropathic pain, suppressing neuropathic pain, and alleviating the symptoms of neuropathic pain. The term "patient" is intended to include those mammals, such as humans, that are in need of treatment or disease prevention, that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

The crystalline compound of the invention can be synthesized from readily available starting materials as described below and in the Examples. It will be appreciated that where typical or preferred process conditions (i.e., reaction temperatures, times, mole ratios of reactants, solvents, pressures, etc.) are given, other process conditions can also be used unless otherwise stated. It will be appreciated that while specific process conditions (i.e. crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 25° C. to about 50° C. In other instances, reactions or crystallizations were conducted at room temperature and the temperature was actually measured and recorded.

Generally, the crystallization is conducted in a suitable inert diluent or solvent system, examples of which include, but are not limited to, methanol, ethanol, isopropanol, isobutanol, ethyl acetate, acetonitrile, dichloromethane, methyl t-butyl ether, and the like, and mixtures thereof, optionally containing water. Upon completion of the crystallization, the crystalline compound can be isolated from the reaction mixture by any conventional means such as precipitation, concentration, centrifugation and the like.

The 4-[2-(2,4,6-trifluorophenoxymethyl)phenyl]piperidine employed in the invention can be readily prepared from commercially available starting materials and reagents using the procedures described in the Examples. The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

In general, the crystalline compound of the invention can be prepared by treating 4-[2-(2,4,6-trifluorophenoxymethyl)phenyl]piperidine with an inert diluent to complete dissolution. Suitable inert diluents include by way of illustration and not limitation, acetone, acetonitrile, ethyl acetate, methyl ethyl ketone, methanol, ethanol, isopropanol, water, and so forth. Other suitable inert diluents include by way of illustration and not limitation, combinations of inert diluents such as acetone with water, acetonitrile with water, ethanol and ethyl acetate, methanol and water, and isopropanol and water. In one particular embodiment, the inert diluent is ethyl acetate or a combination of isopropanol with water. Generally, dissolution is conducted at a temperature ranging from about 50° C. to about 90° C., in one embodiment at a temperature ranging from about 60-80° C., and in another embodiment at a temperature ranging from about 65-75° C. The solution is then cooled to form the crystalline compound of the invention. In one particular embodiment, the solution is cooled to about 20-30° C. such as 25° C. After a suitable amount of time, crystals will be observed. In one embodiment, crystals are observed after a period of about 1 hour. After crystals are observed, the volume of the mother liquor can be reduced and the crystals isolated and dried. In one embodiment, once crystals are observed, crystals are allowed to develop for a period of about 12-24 hours prior to isolation.

In one embodiment, the crystalline compound of the invention is prepared by treating the hydrochloride salt 4-[2-(2,4,6-trifluorophenoxymethyl)phenyl]piperidine with ethyl acetate and ethanol to complete dissolution and cooling to effect crystallization. The crystals are then isolated to yield a crystalline hydrochloride salt having purity typically greater than 99%. Typically, this process can be conducted at any of the aforementioned temperature ranges. For example, dissolution can be done at about 65-70° C., followed by cooling to room temperature.

The same crystalline form can be prepared with a slightly higher purity and better hydroscopic properties by recrystallization. Thus, in another embodiment, the crystalline hydrochloride salt prepared using ethyl acetate and ethanol is recrystallized with isopropanol and water, i.e., treated with isopropanol and water to complete dissolution and cooled to effect crystallization. The resulting solids can then be isolated and dried to yield the crystalline compound of the invention. Typically, this process can be conducted at any of the aforementioned temperature ranges. For example, dissolution can be done at about 75° C., followed by cooling to room temperature. The volume ratio of isopropanol to water will typically be in the range of about 9:1 to about 21:1, for example, in one embodiment about 10:1 and in another embodiment about 20:1.

The hydrochloride salt starting material can be prepared by techniques that are well known in the art, and examples are provided in the Examples herein. For example, 4-[2-(2,4,6-trifluorophenoxymethyl)phenyl]piperidine-1-carboxylic acid t-butyl ester can be deprotected using hydrochloric acid in ethanol to yield the hydrochloride salt.

Crystalline Properties

Among other advantages, it has been discovered that forming a crystalline hydrochloride salt of 4-[2-(2,4,6-trifluorophenoxymethyl)phenyl]piperidine, is useful for purifying the compound itself. For example, the crystalline hydrochloride salt of the invention has a purity of greater than 99.0%.

As is well known in the field of powder x-ray diffraction, relative peak heights of PXRD spectra are dependent on a number of factors relating to sample preparation and instrument geometry, while peak positions are relatively insensitive to experimental details. A PXRD pattern was obtained as set forth in Example 4. Thus, in one embodiment, the crystalline compound of the invention is characterized by a PXRD pattern having certain peak positions.

The crystalline compound is characterized by a PXRD pattern in which the peak positions are substantially in accordance with those shown in FIG. 1. Those peaks are listed below, in order of descending relative intensity. All PXRD peak intensities were corrected by subtracting the corresponding background intensity for each peak.

| I % | 2-Theta | I % | 2-Theta |
|---|---|---|---|
| 100 | 17.16 | 30 | 27.24 |
| 66 | 16.06 | 26 | 29.60 |
| 55 | 10.22 | 16 | 4.44 |
| 51 | 26.32 | 24 | 31.94 |
| 43 | 18.38 | 19 | 23.76 |
| 33 | 21.78 | 22 | 8.11 |
| 32 | 13.18 | | |

Thus, in one embodiment, the crystalline compound is characterized by a powder x-ray diffraction (PXRD) pattern comprising diffraction peaks at 2θ values of 4.44±0.20, 10.22±0.20, 17.16±0.20, and 21.78±0.20; and further characterized by having one or more additional diffraction peaks at 2θ values selected from 8.11±0.20, 13.18±0.20, 16.06±0.20, 18.38±0.20, 23.76±0.20, 26.32±0.20, 27.24±0.20, 29.60±0.20, and 31.94±0.20.

Figure 2:
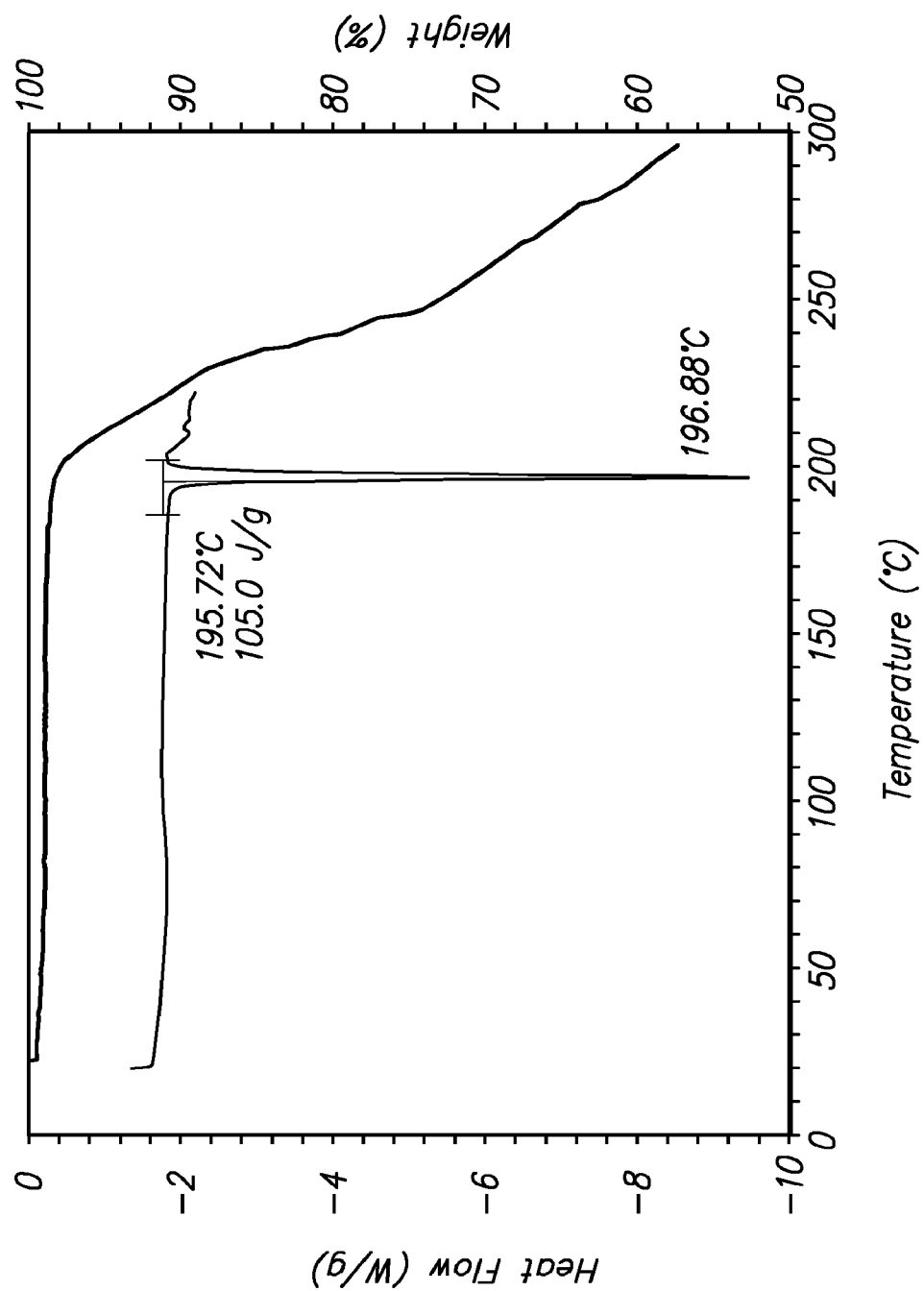
FIG. 2 shows a differential scanning calorimetry (DSC) thermograph and a thermal gravimetric analysis (TGA) trace.

A differential scanning calorimetry (DSC) trace was obtained as set forth in Example 5. Thus, in one embodiment, the crystalline compound is characterized by its DSC thermograph. In one embodiment, the crystalline compound is characterized by a DSC thermograph which shows a melting point of about 196.9° C., with no significant thermal decomposition below about 200.0° C., as seen in FIG. 2.

Thermogravimetric analysis (TGA) was performed on the crystalline compound as described in Example 5. Thus, in one embodiment, the crystalline compound is characterized by its TGA trace. In one embodiment, the crystalline compound is characterized by a TGA trace which shows a loss of solvents and/or water (about 0.5%) at temperatures below about 150.0° C., as seen in FIG. 2.

Figure 3:
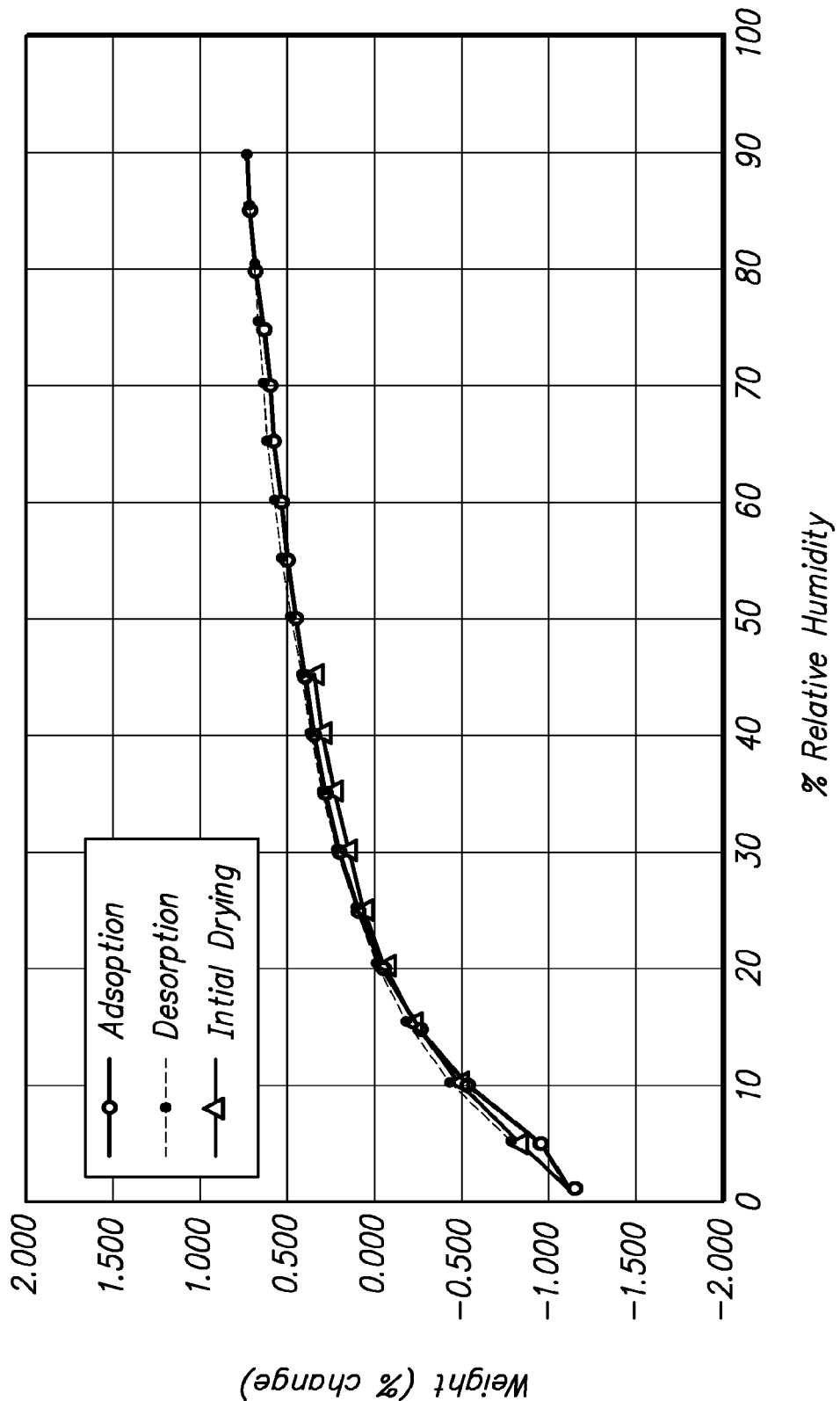
FIG. 3 shows a dynamic moisture sorption (DMS) profile.
Figure 4:
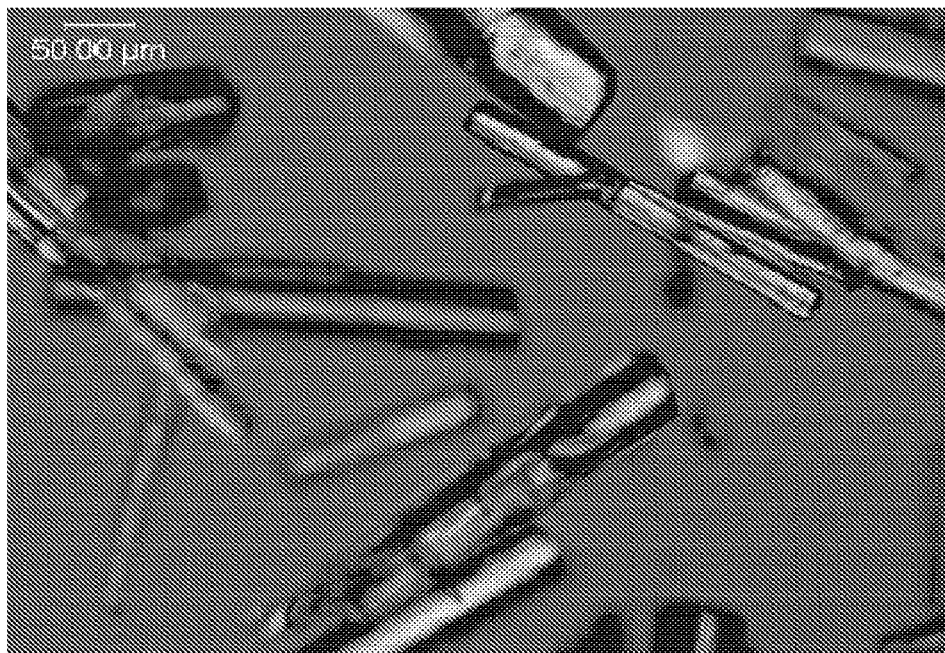
FIG. 4 is a micrographic image.

The crystalline compound of the invention has been demonstrated to have a reversible sorption/desorption profile with acceptable levels of hygroscopicity. For example, the crystalline compound has no or minimal hygroscopicity propensity, and has exhibited less than about 2.0% weight gain when exposed to up to 90% relative humidity, as seen in FIG. 3.

These properties of the crystalline compound of the invention are further illustrated in the Examples below.

Utility

4-[2-(2,4,6-Trifluorophenoxymethyl)phenyl]piperidine possesses serotonin and norepinephrine reuptake inhibitory activity. Thus, this compound, as well as of the crystalline compound of the invention, is expected to have therapeutic utility as a combined serotonin and norepinephrine reuptake inhibitor (SNRI).

The inhibition constant ($K_i$) of a compound is the concentration of competing ligand in a competition assay that would occupy 50% of the transporters if no radioligand were present. $K_i$ values can be determined from radioligand competition binding studies with $^3$H-nisoxetine (for the norepinephrine transporter, NET) and $^3$H-citalopram (for the serotonin transporter, SERT), as described in Assay 1. These $K_i$ values are derived from $IC_{50}$ values in the binding assay using the Cheng-Prusoff equation and the $K_d$ of the radioligand (Cheng & Prusoff (1973) *Biochem. Pharmacol.* 22(23):3099-3108). Functional $IC_{50}$ values can be determined in the functional inhibition of uptake assays described in Assay 2. These $IC_{50}$ values can be converted to $K_i$ values using the Cheng-Prusoff equation and the $K_m$ of the transmitter for the transporter. It is noted however, that the uptake assay conditions described in Assay 2 are such that the $IC_{50}$ values are very close to the $K_i$ values, should a mathematical conversion be desired, since the neurotransmitter concentration (5-HT or NE) used in the assay is well below its $K_m$ for the respective transporter.

Exemplary assays to determine the serotonin and/or norepinephrine reuptake inhibiting activity of the crystalline compound of the invention include by way of illustration and not limitation, assays that measure SERT and NET binding, for example, as described in Assay 1. In addition, it is useful to understand the level of DAT binding and uptake in an assay such as that described in Assay 1. Useful secondary assays include neurotransmitter uptake assays to measure competitive inhibition of serotonin and norepinephrine uptake into cells expressing the respective human or rat recombinant transporter (hSERT, hNET, or hDAT) as described in Assay 2, and ex vivo radioligand binding and neurotransmitter uptake assays that are used to determine the in vivo occupancy of SERT, NET and DAT in tissue as described in Assay 3. Other assays that are useful to evaluate pharmacological properties include those listed in Assay 4. Exemplary in vivo assays include the formalin paw test described in Assay 5, which is a reliable predictor of clinical efficacy for the treatment of neuropathic pain, and the spinal nerve ligation model described in Assay 6. The aforementioned assays are useful in determining the therapeutic utility, for example, the neuropathic pain relieving activity, of the crystalline compound of the invention. Other properties and utilities of the crystalline compound of the invention can be demonstrated using various in vitro and in vivo assays well-known to those skilled in the art.

The crystalline compound of the invention is expected to be useful for the treatment and/or prevention of medical conditions in which the regulation of monoamine transporter function is implicated, in particular those conditions mediated by or responsive to the inhibition of serotonin and norepinephrine reuptake. Thus it is expected that patients suffering from a disease or disorder that is treated by the inhibition of the serotonin and/or the norepinephrine transporter can be treated by administering a therapeutically effective amount of the crystalline compound of the invention. Such medical conditions include, by way of example, pain disorders such as neuropathic pain, fibromyalgia, and chronic pain, depressive disorders such as major depression, affective disorders such as an anxiety disorder, attention deficit hyperactivity disorder, cognitive disorders such as dementia, and stress urinary incontinence.

The amount of active agent administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the active agent and any secondary agents being administered, and the like. Treatment of a patient suffering from a disease or medical condition (such as neuropathic pain) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating neuropathic pain, a measure of the effectiveness of treatment may involve assessment of the patient's quality of life, e.g., improvements in the patient's sleeping patterns, work attendance, ability to exercise and be ambulatory, etc. Pain scales, operating on a point basis, may also be used to help evaluate a patient's pain level. Indicators for the other diseases and conditions described herein, are well-known to those skilled in the art, and are readily available to the treating physician. Continuous monitoring by the physician will insure that the optimal amount of active agent will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Pain Disorders

SNRIs have been shown to have a beneficial effect on pain such as painful diabetic neuropathy (duloxetine, Goldstein et al. (2005) *Pain* 116:109-118; venlafaxine, Rowbotham et al. (2004) *Pain* 110:697-706), fibromyalgia (duloxetine, Russell et al. (2008) *Pain* 136(3):432-444; milnacipran, Vitton et al. (2004) *Human Psychopharmacology* 19:S27-S35), and migraine (venlafaxine, Ozyalcin et al. (2005) *Headache* 45(2):144-152). Thus, one embodiment of the invention relates to a method for treating a pain disorder, comprising administering to a patient a therapeutically effective amount of the crystalline compound of the invention. Typically, the therapeutically effective amount will be the amount that is sufficient to relieve the pain. Exemplary pain disorders include, by way of illustration, acute pain, persistent pain, chronic pain, inflammatory pain, and neuropathic pain. More specifically, these include pain associated with or caused by: arthritis; back pain including chronic low back pain; cancer, including tumor related pain (e.g., bone pain, headache, facial pain or visceral pain) and pain associated with cancer therapy (e.g., post-chemotherapy syndrome, chronic post-surgical pain syndrome and post-radiation syndrome); carpal tunnel syndrome; fibromyalgia; headaches including chronic tension headaches; inflammation associated with polymyalgia, rheumatoid arthritis and osteoarthritis; migraine; neuropathic pain including complex regional pain syndrome; overall pain; post-operative pain; shoulder pain; central pain syndromes, including post-stroke pain, and pain associated with spinal cord injuries and multiple sclerosis; phantom limb pain; pain associated with Parkinson's disease; and visceral pain (e.g., irritable bowel syndrome). Of particular interest is the treatment of neuropathic pain, which includes diabetic peripheral neuropathy (DPN), HIV-related neuropathy, post-herpetic neuralgia (PHN), and chemotherapy-induced peripheral neuropathy. When used to treat pain disorders such as neuropathic pain, compounds of the invention may be administered in combination with other therapeutic agents, including anticonvulsants, antidepressants, muscle relaxants, NSAIDs, opioid agonists, opioid antagonists, selective serotonin reuptake inhibitors, sodium channel blockers, and sympatholytics. Exemplary compounds within these classes are described herein.

Depressive Disorders

Another embodiment of the invention relates to a method of treating a depressive disorder, comprising administering to a patient a therapeutically effective amount of the crystalline compound of the invention. Typically, the therapeutically effective amount will be the amount that is sufficient to alleviate depression and provide a sense of general well-being. Exemplary depressive disorders include, by way of illustration and not limitation: depression associated with Alzheimer's disease, bipolar disorder, cancer, child abuse, infertility, Parkinson's disease, postmyocardial infarction, and psychosis; dysthymia; grumpy or irritable old man syndrome; induced depression; major depression; pediatric depression; postmenopausal depression; post partum depression; recurrent depression; single episode depression; and subsyndromal symptomatic depression. Of particular interest is the treatment of major depression. When used to treat depressive disorders, compounds of the invention may be administered in combination with other therapeutic agents, including antidepressants and dual serotonin-norepinephrine reuptake inhibitors. Exemplary compounds within these classes are described herein.

Affective Disorders

Another embodiment of the invention relates to a method of treating an affective disorder, comprising administering to a patient a therapeutically effective amount of the crystalline compound of the invention. Exemplary affective disorders include, by way of illustration and not limitation: anxiety disorders such as general anxiety disorder; avoidant personality disorder; eating disorders such as anorexia nervosa, bulimia nervosa and obesity; obsessive compulsive disorder; panic disorder; personality disorders such as avoidant personality disorder and attention deficit hyperactivity disorder (ADHD); post-traumatic stress syndrome; phobias such as agoraphobia, as well as simple and other specific phobias, and social phobia; premenstrual syndrome; psychotic disorders, such as schizophrenia and mania; seasonal affective disorder; sexual dysfunction, including premature ejaculation, male impotence, and female sexual dysfunction such as female sexual arousal disorder; social anxiety disorder; and substance abuse disorders, including chemical dependencies such as addictions to alcohol, benzodiazepines, cocaine, heroin, nicotine and phenobarbital, as well as withdrawal syndromes that may arise from these dependencies. When used to treat affective disorders, compounds of the invention may be administered in combination with other therapeutic agents, including antidepressants. Exemplary compounds within these classes are described herein.

Atomoxetine, which is 10-fold NET selective, is approved for attention deficit hyperactivity disorder (ADHD) therapy, and clinical studies have shown that the SNRI, venlafaxine, can also have a beneficial effect in treating ADHD (Mukaddes et al. (2002) *Eur. Neuropsychopharm.* 12(Supp 3):421). Thus, the crystalline compound of the invention is also expected to be useful in methods for treating attention deficit hyperactivity disorder by administering to a patient a therapeutically effective amount of the crystalline compound of the invention. When used to treat depression, the crystalline compound of the invention may be administered in combination with other therapeutic agents, including antidepressants. Exemplary compounds within these classes are described herein.

Cognitive Disorders

Another embodiment of the invention relates to a method of treating a cognitive disorder, comprising administering to a patient a therapeutically effective amount of the crystalline compound of the invention. Exemplary cognitive disorders include, by way of illustration and not limitation: dementia, which includes degenerative dementia (e.g., Alzheimer's disease, Creutzfeldt-Jakob disease, Huntingdon's chorea, Parkinson's disease, Pick's disease, and senile dementia), vascular dementia (e.g., multi-infarct dementia), and dementia associated with intracranial space occupying lesions, trauma, infections and related conditions (including HIV infection), metabolism, toxins, anoxia and vitamin deficiency; and mild cognitive impairment associated with ageing, such as age associated memory impairment, amnesiac disorder and age-related cognitive decline. When used to treat cognitive disorders, the crystalline compound of the invention may be administered in combination with other therapeutic agents, including anti-Alzheimer's agents and anti-Parkinson's agents. Exemplary compounds within these classes are described herein.

Other Disorders

SNRIs have also been shown to be effective for the treatment of stress urinary incontinence (Dmochowski (2003) *Journal of Urology* 170(4): 1259-1263). Thus, another embodiment of the invention relates to a method for treating stress urinary incontinence, comprising administering to a patient a therapeutically effective amount of the crystalline compound of the invention. When used to treat stress urinary incontinence, compounds of the invention may be administered in combination with other therapeutic agents, including anticonvulsants. Exemplary compounds within these classes are described herein.

Duloxetine, an SNRI, is undergoing clinical trials for evaluating its efficacy in treating chronic fatigue syndrome, and has recently been shown to be effective in treating fibromyalgia (Russell et al. (2008) *Pain* 136(3):432-444). The crystalline compound of the invention, due to its expected ability to inhibit SERT and NET, is also expected to have this utility, and another embodiment of the invention relates to a method for treating chronic fatigue syndrome, comprising administering to a patient a therapeutically effective amount of the crystalline compound of the invention.

Sibutramine, a norepinephrine and dopamine reuptake inhibitor, has been shown to be useful in treating obesity (Wirth et al. (2001) *JAMA* 286(11):1331-1339). The crystalline compound of the invention, due to its expected ability to inhibit NET, is also expected to have this utility, and another embodiment of the invention relates to a method for treating obesity, comprising administering to a patient a therapeutically effective amount of the crystalline compound of the invention.

Desvenlafaxine, an SNRI, has been shown to relieve vasomotor symptoms associated with menopause (Deecher et al. (2007) *Endocrinology* 148(3):1376-1383). The crystalline compound of the invention, due to its expected ability to inhibit SERT and NET, is also expected to have this utility, and another embodiment of the invention relates to a method for treating vasomotor symptoms associated with menopause, comprising administering to a patient a therapeutically effective amount of the crystalline compound of the invention.

Research Tools

Since the crystalline compound of the invention is expected to possess both serotonin reuptake inhibition activity and norepinephrine reuptake inhibition activity, this compound is also expected to find utility as a research tool for investigating or studying biological systems or samples having serotonin or norepinephrine transporters. Any suitable biological system or sample having serotonin and/or norepinephrine transporters may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, serotonin reuptake in a mammal is inhibited by administering a serotonin reuptake-inhibiting amount of the crystalline compound of the invention. In another particular embodiment, norepinephrine reuptake in a mammal is inhibited by administering a norepinephrine reuptake-inhibiting amount of the crystalline compound of the invention. The crystalline compound of the invention can also be used as a research tool by conducting biological assays using such compound.

When used as a research tool, a biological system or sample comprising a serotonin transporter and/or a norepinephrine transporter is typically contacted with a serotonin reuptake-inhibiting or norepinephrine reuptake-inhibiting amount of the crystalline compound of the invention. After the biological system or sample is exposed to the compound, the effects of inhibiting serotonin reuptake and/or norepinephrine reuptake are determined using conventional procedures and equipment. Exposure encompasses contacting cells or tissue with the compound, administering the compound to a mammal, for example by i.p. or i.v. administration, and so forth. This determining step may comprise measuring a response, i.e., a quantitative analysis or may comprise an observation, i.e., a qualitative analysis. Measuring a response involves, for example, determining the effects of the compound on the biological system or sample using conventional procedures and equipment, such as serotonin and norepinephrine reuptake assays. The assay results can be used to determine the activity level as well as the amount of compound necessary to achieve the desired result, i.e., a serotonin reuptake-inhibiting and a norepinephrine reuptake-inhibiting amount.

Additionally, the crystalline compound of the invention can be used as a research tool for evaluating other chemical compounds, and thus is also useful in screening assays to discover, for example, new compounds having both serotonin reuptake-inhibiting activity and norepinephrine reuptake-inhibiting activity. In this manner, the crystalline compound of the invention is used as a standard in an assay to allow comparison of the results obtained with a test compound and with the crystalline compound of the invention to identify those test compounds that have about equal or superior reuptake-inhibiting activity, if any. For example, reuptake data for a test compound or a group of test compounds is compared to the reuptake data for the crystalline compound of the invention to identify those test compounds that have the desired properties, e.g., test compounds having reuptake-inhibiting activity about equal or superior to the crystalline compound of the invention, if any. This aspect of the invention includes, as separate embodiments, both the generation of comparison data (using the appropriate assays) and the analysis of the test data to identify test compounds of interest. Thus, a test compound can be evaluated in a biological assay, by a method comprising the steps of: (a) conducting a biological assay with a test compound to provide a first assay value; (b) conducting the biological assay with the crystalline compound of the invention to provide a second assay value; wherein step (a) is conducted either before, after or concurrently with step (b); and (c) comparing the first assay value from step (a) with the second assay value from step (b). Exemplary biological assays include serotonin and norepinephrine reuptake assays.

Pharmaceutical Compositions and Formulations

The crystalline compound of the invention is typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration. However, it will be understood by those skilled in the art that, once the crystalline compound of the invention has been formulated, it may no longer be in crystalline form, i.e., it may be dissolved in a suitable carrier. Further, the crystalline compound of the invention may be administered, for example orally, in multiple doses per day (e.g., twice, three times or four times daily), in a single daily dose, in a twice daily dose, in a single weekly dose, and so forth.

Accordingly, in one embodiment, the invention relates to a pharmaceutical composition comprising a pharmaceutically acceptable carrier and the crystalline compound of the invention. The compositions may contain other therapeutic and/or formulating agents if desired. When discussing compositions, the "crystalline compound of the invention" may also be referred to herein as the "active agent," to distinguish it from other components of the formulation, such as the carrier.

Pharmaceutical compositions of the invention typically contain a therapeutically effective amount of the crystalline compound of the invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent. In one exemplary embodiment, a pharmaceutical composition contains from about 1 to 20 mg of active agent, including from about 1 to 15 mg of active agent and from about 1 to 10 mg of active agent. In another exemplary embodiment, a pharmaceutical composition contains from about 5 to 20 mg of active agent, including from about 7.5 to 15 mg of active agent. For example the active agent may be formulated in 1 mg and 10 mg unit doses.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers, and the like, using conventional procedures and equipment.

In one embodiment, the pharmaceutical compositions are suitable for oral administration. One exemplary dosing regimen would be an oral dosage form administered once or twice daily. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills, and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate, sodium sulfite, and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, i.e., each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, and glycerin. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

The crystalline compound of the invention can also be administered parenterally (e.g., by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agent. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

The crystalline compound of the invention can also be administered transdermally using known transdermal delivery systems and excipients. For example, the compound can be admixed with permeation enhancers, such as propylene glycol, polyethylene glycol monolaurate, azacycloalkan-2-ones, and the like, and incorporated into a patch or similar delivery system. Additional excipients including gelling agents, emulsifiers and buffers, may be used in such transdermal compositions if desired.

If desired, the crystalline compound of the invention may be administered in combination with one or more other therapeutic agents. Thus, in one embodiment, compositions of the invention may optionally contain other drugs that are co-administered with the crystalline compound of the invention. For example, the composition may further comprise one or more drugs (also referred to as "secondary agents(s)") selected from the group of anti-Alzheimer's agents, anticonvulsants (antiepileptics), antidepressants, anti-Parkinson's agents, dual scrotonin-norepinephrine reuptake inhibitors (SNRIs), non-steroidal anti-inflammatory agents (NSAIDs), norepinephrine reuptake inhibitors, opioid agonists (opioid analgesics), opioid antagonists, selective serotonin reuptake inhibitors, sodium channel blockers, sympatholytics, and combinations thereof. Numerous examples of such therapeutic agents are well known in the art, and examples are described herein. By combining the crystalline compound of the invention with a secondary agent, triple therapy can be achieved, i.e., serotonin reuptake inhibitory activity, norepinephrine reuptake inhibitory activity, and activity associated with the secondary agent (e.g., antidepressant activity), using only two active components. Since pharmaceutical compositions containing two active components are typically easier to formulate than compositions containing three active components, such two-component compositions provide a significant advantage over compositions containing three active components. Accordingly, in yet another aspect of the invention, a pharmaceutical composition comprises the crystalline compound of the invention, a second active agent, and a pharmaceutically acceptable carrier. Third, fourth, etc., active agents may also be included in the composition. In combination therapy, the amount of compound of the invention that is administered, as well as the amount of secondary agents, may be less than the amount typically administered in monotherapy.

The crystalline compound of the invention may be either physically mixed with the second active agent to form a composition containing both agents; or each agent may be present in separate and distinct compositions which are administered to the patient simultaneously or sequentially. For example, the crystalline compound of the invention can be combined with a second active agent using conventional procedures and equipment to form a combination of active agents comprising the crystalline compound of the invention and a second active agent. Additionally, the active agents may be combined with a pharmaceutically acceptable carrier to form a pharmaceutical composition comprising the crystalline compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, the crystalline compound of the invention can be orally administered simultaneously or sequentially with another active agent using two tablets, with one tablet for each active agent, where sequential may mean being administered immediately after administration of the compound of the invention or at some predetermined time later (e.g., one hour later or three hours later). Alternatively, the combination may be administered by different routes of administration, i.e., one orally and the other by inhalation.

In one embodiment, the kit comprises a first dosage form comprising the crystalline compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount, i.e., are typically administered in an amount that produces a therapeutically beneficial effect when co-administered with the crystalline compound of the invention. The secondary agent can be in the form of a pharmaceutically acceptable salt, solvate, optically pure stereoisomer, and so forth. Thus, secondary agents listed below are intended to include all such forms, and are commercially available or can be prepared using conventional procedures and reagents.

Representative anti-Alzheimer's agents include, but are not limited to: donepezil, galantamine, memantine, rivastigmine, selegiline, tacrine, and combinations thereof.

Representative anticonvulsants (antiepileptics) include, but are not limited to: acetazolamide, albutoin, 4-amino-3-hydroxybutyric acid, beclamide, carbamazepine, cinromide, clomethiazole, clonazepam, diazepam, dimethadione, eterobarb, ethadione, ethosuximide, ethotoin, felbamate, fosphenytoin, gabapentin, lacosamide, lamotrigine, lorazepam, magnesium bromide, magnesium sulfate, mephenytoin, mephobarbital, methsuximide, midazolam, nitrazepam, oxazepam, oxcarbazepine, paramethadione, phenacemide, pheneturide, phenobarbital, phensuximide, phenytoin, potassium bromide, pregabalin, primidone, progabide, sodium bromide, sodium valproate, sulthiame, tiagabine, topiramate, trimethadione, valproic acid, valpromide, vigabatrin, zonisamide, and combinations thereof. In a particular embodiment, the anticonvulsant is selected from carbamazepine, gabapentin, pregabalin, and combinations thereof.

Representative antidepressants include, but are not limited to: adinazolam, amitriptyline, clomipramine, desipramine, dothiepin (e.g., dothiepin hydrochloride), doxepin, imipramine, lofepramine, mirtazapine, nortriptyline, protriptyline, trimipramine, venlafaxine, zimelidine, and combinations thereof.

Representative anti-Parkinson's agents include, but are not limited to: amantadine, apomorphine, benztropine, bromocriptine, carbidopa, diphenhydramine, entacapone, levodopa, pergolide, pramipexole, ropinirole, selegiline, tolcapone, trihexyphenidyl, and combinations thereof.

Representative dual serotonin-norepinephrine reuptake inhibitors (SNRIs) include, but are not limited to: bicifadine, desvenlafaxine, duloxetine, milnacipran, nefazodone, venlafaxine, and combinations thereof.

Representative non-steroidal anti-inflammatory agents (NSAIDs) include, but are not limited to: acemetacin, acetaminophen, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lomoxicam, meclofenamate, meclofenamic acid, mefenamic acid, meloxicam, mesalamine, miroprofen, mofebutazone, nabumetone, naproxen, niflumic acid, nimesulide, nitroflurbiprofen, olsalazine, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof. In a particular embodiment, the NSAID is selected from ibuprofen, indomethacin, nabumetone, naproxen (for example, naproxen sodium), and combinations thereof.

Representative muscle relaxants include, but are not limited to: carisoprodol, chlorzoxazone, cyclobenzaprine, diflunisal, metaxalone, methocarbamol, and combinations thereof.

Representative norepinephrine reuptake inhibitors include, but are not limited to: atomoxetine, buprorion and the buprorion metabolite hydroxybuproprion, maprotiline, reboxetine (for example, (S,S)-reboxetine), viloxazine, and combinations thereof. In a particular embodiment, the norepinephrine reuptake inhibitor is selected from atomoxetine, reboxetine, and combinations thereof.

Representative opioid agonists (opioid analgesics) and antagonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid agonist is selected from codeine, dihydrocodeine, hydrocodone, hydromorphone, morphine, oxycodone, oxymorphone, tramadol, and combinations thereof.

Representative selective serotonin reuptake inhibitors (SSRIs) include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof. In certain embodiments, the SSRI is selected from citalopram, paroxetine, sertraline, and combinations thereof.

Representative sodium channel blockers include, but are not limited to: carbamazepine, fosphenytoin, lamotrignine, lidocaine, mexiletine, oxcarbazepine, phenytoin, and combinations thereof.

Representative sympatholytics include, but are not limited to: atenolol, clonidine, doxazosin, guanethidine, guanfacine, modafinil, phentolamine, prazosin, reserpine, tolazoline (e.g., tolazoline hydrochloride), tamsulosin, and combinations thereof.

The following formulations illustrate representative pharmaceutical compositions of the present invention:

Exemplary Hard Gelatin Capsules for Oral Administration

The crystalline compound of the invention (50 g), spray-dried lactose (440 g) and magnesium stearate (10 g) are thoroughly blended. The resulting composition is then loaded into hard gelatin capsules (500 mg of composition per capsule).

Alternately, the crystalline compound (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

The crystalline compound of the invention (100 mg) is thoroughly blended with polyoxyethylene sorbitan monooleate (50 mg) and starch powder (250 mg). The mixture is then loaded into a gelatin capsule (400 mg of composition per capsule).

Alternately, the crystalline compound (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

The crystalline compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, the crystalline compound (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, the crystalline compound (400 mg) is thoroughly blended with cornstarch (50 mg), croscarmellose sodium (25 mg), lactose (120 mg), and magnesium stearate (5 mg). The mixture is then compressed to form a single-scored tablet (600 mg of compositions per tablet).

Exemplary Suspension Formulation for Oral Administration

The following ingredients are mixed to form a suspension containing 100 mg of active agent per 10 mL of suspension:

| Ingredients | Amount |
| --- | --- |
| Crystalline compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Injectable Formulation for Administration by Injection

The crystalline compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

The crystalline compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, the crystalline compound (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the crystalline compound per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning:
AcOH acetic acid
BSA bovine serum albumin
DCM dichloromethane (i.e., methylene chloride)
DIAD diisopropyl azodicarboxylate
DIPEA N,N-diisopropylethylamine
DMEM Dulbecco's Modified Eagle's Medium
DMSO dimethylsulfoxide
EDTA ethylenediaminetetraacetic acid
EtOAc ethyl acetate
EtOH ethanol
FBS fetal bovine serum
hDAT human dopamine transporter
HEPES 4-(2-hydroxyethyl)-1-piperazineethanesulfonic acid
hNET human norepinephrine transporter
hSERT human serotonin transporter
5-HT 5-hydroxytryptamine
IPA isopropyl alcohol
IPAc isopropyl acetate
MeCN acetonitrile ($CH_3CN$)
MeOH methanol
NA noradrenaline
PBS phosphate buffered saline
$PPh_3$ triphenylphosphine
TFA trifluoroacetic acid
THF tetrahydrofuran
TsCl p-toluenesulfonyl chloride or 4-methylbenzenesulfonyl chloride Any other abbreviations used herein but not defined have their standard, generally accepted meaning. Unless noted otherwise, all materials, such as reagents, starting materials and solvents, were purchased from commercial suppliers (such as Sigma-Aldrich, Fluka Riedel-de Haën, and the like) and were used without further purification.

Preparation 1

4-(2-Methanesulfonyloxymethlphenyl)piperidine-1-carboxylic Acid t-Butyl Ester

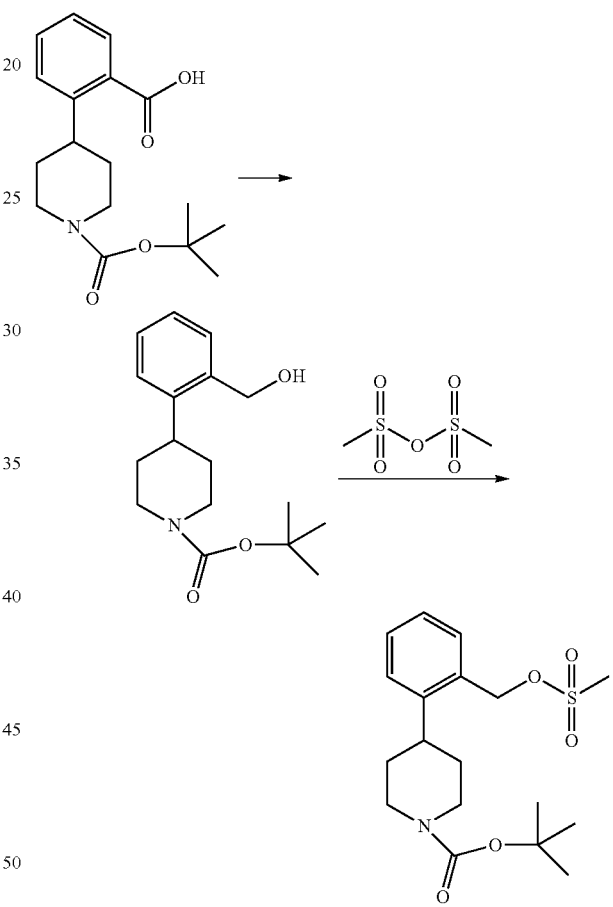

4-(2-Carboxyphenyl)piperidine-1-carboxylic acid t-butyl ester (5.0 g, 160 mmol, 1.0 eq.) and THF (100 mL, 1.0 mol) were combined at room temperature under nitrogen. 1.0M Borane-THF complex in THF (32.7 mL, 32.7 mmol, 2.0 eq.) was added dropwise over 10 minutes (5° C. exotherm, gas evolution). The mixture was stirred at room temperature for 5 minutes, then heated at 50° C. for 1 hour. The mixture was cooled to room temperature, and the reaction was quenched slowly with MeOH (30 mL) (mild exotherm, significant gas evolution), then concentrated by rotary evaporation. The material was azeotroped with MeOH (2×50 mL). The crude product was dissolved in EtOAc (100 mL, 1 mol), washed with $NaHCO_3$ (50 mL), then saturated aqueous NaCl (50 mL). The organic layer was dried over anhydrous $Na_2SO_4$, filtered, and concentrated in vacuo to yield 4-(2-hydroxymethylphenyl)piperidine-1-carboxylic acid t-butyl ester (4.4 g) as a clear, light yellow oil that solidified upon sitting.

4-(2-Hydroxymethylphenyl)piperidine-1-carboxylic acid t-butyl ester (50.0 g, 172 mmol, 1.0 eq.) was dissolved in DCM (500 mL, 8000 mmol). The mixture was cooled at 0° C. under nitrogen and methanesulfonic anhydride (44.8 g, 257 mmol, 1.5 eq.) was added in one portion. DIPEA (47.8 mL, 274 mmol, 1.6 eq.) was added dropwise over 5 minutes and the mixture was stirred at 0° C. for 90 minutes. Water (400 mL, 20 mol) was added and the mixture was stirred for 5 minutes. The phases were separated, and the organic layer was washed with water (300 mL), dried over $Na_2SO_4$, and the solvent removed to yield the title compound (70 g) as a thick oil, which was used without further purification.

$^1$H NMR (400 MHz, DMSO-$d_6$) δ (ppm) 7.37-7.43 (m, 3H), 7.31 (d, 1H), 7.22 (m, 2H), 5.38 (s, 2H), 4.28 (m, 2H), 2.92-3.10 (m, 1H), 2.92 (s, 3H), 2.80-2.92 (m, 2H), 1.63-1.81 (m, 4H), 1.51 (s, 9H).

EXAMPLE 1

Crystalline Hydrochloride Salt of 4-[2-(2,4,6-Trifluorophenoxymethyl)phenyl]piperidine

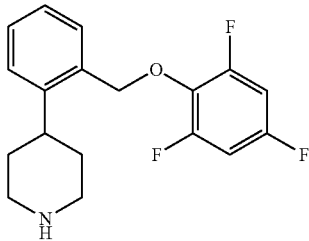 [SMILES: Fc1cc(F)c(OCc2ccccc2C2CCNCC2)c(F)c1]

4-(2-Methanesulfonyloxymethylphenyl)piperidine-1-carboxylic acid t-butyl ester (27.0 g, 60.6 mmol, 1.0 eq.) was dissolved in MeCN (540 mL) and added to $K_2CO_3$ (25 g, 180 mmol, 3.0 eq.) and 2,4,6-trifluorophenol (13.5 g, 90.9 mmol, 1.5 eq.). The mixture was vigorously stirred at 50° C. for 6 hours, removed from the heat, and stirred overnight. The mixture was cooled at room temperature, and diluted with EtOAc (700 mL) and water (700 mL). The phases were separated, and the organic layer was washed twice with 1.0 M NaOH in water (2×400 mL) and saturated aqueous NaCl (1×400 mL), then dried over $Na_2SO_4$ and the solvent removed to yield crude 4-[2-(2,4,6-trifluorophenoxymethyl)-phenyl]piperidine-1-carboxylic acid t-butyl ester (25.0 g). The crude product was combined with smaller scale runs for a total of 30 g, and purified by chromatography (0-10% EtOAc in hexanes) to yield 4-[2-(2,4,6-trifluorophenoxymethyl)phenyl]piperidine-1-carboxylic acid t-butyl ester (22.0 g).

The t-butyl ester (22.0 g, 31.3 mmol, 1.0 eq.) was combined with 1.25M HCl in EtOH (250 mL, 310 mmol, 10.0 eq.). The mixture was stirred at room temperature for 8 hours, then stored at −10° C. over approximately 48 hours. Most of solvent was removed by rotary evaporation. To the resulting thick slurry was added EtOAc (80 mL), followed by stirring at room temperature for 2 hours. First crop was isolated by filtration, and the filter cake was washed with EtOAc (20 mL) and dried to yield the title compound as a hydrochloride salt (8.5 g, >99% purity) white solid. HPLC of the filtrate shows ~25% area of product. For the second crop, the solvent was removed by rotary evaporation and the resulting solid (~10 g) was slurried in EtOAc (40 mL), first at room temperature, then at 60° C., and again at room temperature to yield the title compound as a hydrochloride salt (1.7 g, >99% purity).

Two lots of the hydrochloride salt (18.5 g, 51.7 mmol) were combined with EtOAc (75 mL, 770 mmol). The resulting thick but free-flowing slurry was heated at 65° C. for 30 minutes, cooled to room temperature, and filtered. The flask and the filter cake were washed with EtOAc (20 mL), and the solids dried under high vacuum at room temperature overnight to yield the crystalline hydrochloride salt (18.2 g, 99.3% purity).

Good crystallinity was observed by XRPD. LC-MS (2 mg in 2 mL of 1:1 MeCN: 1M aq HCl; API 150EX LC/MS System) was found to be consistent with structure. NMR (DMSO-$d_6$, Varian VnmrJ 400) was found to be consistent with the structure and the salt form.

EXAMPLE 2

Crystalline Hydrochloride Salt of 4-[2-(2,4,6-Trifluorophenoxymethyl)phenyl]piperidine Acetyl chloride (83.5 mL, 1170 mmol) was slowly added to EtOH (140 mL, 2.4 mol). 4-[2-(2,4,6-Trifluorophenoxymethyl)phenyl]piperidine-1-carboxylic acid t-butyl ester (55.0 g, 117 mmol) dissolved in EtOH (100 mL, 2.0 mol) was added and the resulting mixture was stirred at room temperature for 6 hours. Most of solvent was removed by rotary evaporation. To the resulting thick slurry was added EtOAc (300 mL), followed by partial solvent removal to ~100 mL. Fresh EtOAc (200 mL) was added and the resulting slurry was stirred for 1 hour, filtered and dried to yield a hydrochloride salt (28.0 g, ~99% purity). The filtrate was concentrated to a thick paste and IPAc (100 mL) was added, stirred for 1 hour, filtered and dried to further yield 5.0 g of the hydrochloride salt (~99% purity).

Two lots of the hydrochloride salt (83.0 g, 230 mmol, ~99% purity) were combined with EtOAc (250 mL, 2.6 mol). The resulting slurry was heated at 70° C. and then slowly cooled to room temperature, followed by stirring overnight. The resulting free-flowing slurry was filtered and the filter cake was washed with EtOAc (50 mL) then dried under high vacuum for approximately 48 hours to yield a crystalline hydrochloride salt (81.0 g, >99% purity). $^1$H NMR (DMSO-$d_6$, 400 Hz) was found to be consistent with the structure and the salt form of Example 1.

The crystalline hydrochloride salt (50.0 g, 1.40 mol, >99% purity) was dissolved in IPA (250 mL, 3.3 mol), and the resulting slurry was heated to 75° C. Water (25 mL, 1.4 mol) was added. Complete dissolution was observed in 5 minutes, and the internal temperature of the solution was 65° C. The solution was slowly cooled to room temperature and then stirred at room temperature overnight. The resulting solids were filtered and dried under air for 2 hours to yield a semi-dry product. The solids were then dried under high vacuum at room temperature for approximately 48 hours to yield the title crystalline hydrochloride salt (44.1 g, 99.5% purity). The material exhibited good crystallinity by XRPD and DSC.

EXAMPLE 3

Crystalline Hydrochloride Salt of 4-[2-(2,4,6-Trifluorophenoxymethyl)phenyl]piperidine The title crystalline hydrochloride salt (151.1 g, 99.5% purity) was also prepared in a similar manner using 175.0 g of the hydrochloride salt and 10 volumes of 5% water in IPA (total of 90 mL water and 1.8 L IPA).

EXAMPLE 4

Powder X-Ray Diffraction

Powder X-ray diffraction patterns were obtained with a Rigaku Miniflex PXRD diffractometer using Cu Kα (30.0 kV, 15.0 mA) radiation. The analysis was performed with the goniometer running in continuous-scan mode of 2° (2θ) per min with a step size of 0.03° over a range of 2 to 40° in two-theta angle. Samples were prepared on quartz specimen holders as a thin layer of powdered material. The instrument was calibrated with a silicon metal standard, within ±0.02° two-theta angle. A representative PXRD pattern for the crystalline hydrochloride salt of Example 2 is shown in FIG. 1. The samples were hand ground prior to testing, in order to reduce particle size interferences to the relative intensities.

The numerous intense powder diffraction peaks and relatively flat baseline depicted in FIG. 1 strongly indicated that the crystalline hydrochloride salt of Example 2 possessed good crystallinity.

Powder X-ray diffraction patterns were also obtained for the crystalline hydrochloride salt of Example 1 and were found to be consistent with those of the crystalline hydrochloride salt of Example 2.

EXAMPLE 5

Thermal Analysis

Differential scanning calorimetry (DSC) was performed using a TA Instruments Model Q-100 module with a Thermal Analyst controller. Data were collected and analyzed using TA Instruments Thermal Solutions software. A 2.8 mg sample of the crystalline hydrochloride salt of Example 2 was accurately weighed into a covered aluminum pan. After a 5 minute isothermal equilibration period at 22° C., the sample was heated using a linear heating ramp of 10° C./min from 22° C. to 250° C. A representative DSC thermograph is shown in FIG. 2.

The DSC thermograph demonstrates that the crystalline compound of the invention has excellent thermal stability with a melting point at about 196.9° C. and no thermal decomposition below 200.0° C.

A representative TGA trace is shown in FIG. 2, and indicates that a sample of the crystalline form of Example 2 lost a small amount (about 0.5%) of weight from room temperature to 150.0° C., which is consistent with the loss of residual moisture or solvent.

A DSC thermograph and TGA trace were also obtained for the crystalline hydrochloride salt of Example 1 and were found to be consistent with those of the crystalline hydrochloride salt of Example 2.

EXAMPLE 6

Dynamic Moisture Sorption Assessment

A dynamic moisture sorption (DMS) assessment (also known as a moisture sorption-desorption profile) was performed for the crystalline hydrochloride salt of Example 2 using a VTI atmospheric microbalance, SGA-100 system (VTI Corp., Hialeah, Fla. 33016). A sample size of approximately 7.3 mg was used and the humidity was set at the ambient value at the start of the analysis. The DMS analysis consisted of a scan rate of 5% relative humidity/step over the full humidity range of 2% relative humidity to 90% relative humidity. The DMS run was performed isothermally at 25° C. A representative DMS profile is shown in FIG. 3.

The DMS profile demonstrates that the crystalline compound of the invention has a reversible sorption/desorption profile with insignificant hygroscopicity. The crystalline compound has a small weight gain when it exposed to a broad humidity range from 2% relative humidity up to 90% relative humidity, and less than about 2.0% weight gain when exposed to up to 90% relative humidity, which indicates that the crystalline form possesses only a minimal risk of hygroscopicity at ambient conditions.

EXAMPLE 7

Solid State Stability Assessment

A solid-state stability study was initiated with a representative lot of the crystalline hydrochloride salt of 4-[2-(2,4,6-trifluorophenoxymethyl)phenyl]piperidine at −20° C., 5° C., 25° C./60% relative humidity (open container) and 40° C./75% relative humidity (closed and open containers) storage conditions in glass. After 28 days of storage, for the samples kept under all conditions, there was no detectable change in the chemical purity, the chiral purity, PXRD, DSC, and TGA profiles.

EXAMPLE 8

X-ray Structure Analysis of a Single HCl Salt Crystal of 4-[2-(2,4,6-Trifluorophenoxymethyl)phenyl]piperidine A crystalline hydrochloride salt (105.0 mg, >99% purity) was prepared from EtOAc, as described in Example 2. The crystalline hydrochloride salt was then combined with 5 mL of an IPA/water (10% water) solution. The mixture was shaken at room temperature (about 23° C.) until most of the material was dissolved in the solution. The solution was then placed on a heating plate which was pre-heated at 60° C. After 5 minutes, the solution became clear indicating there was no any solid residue in the heated sample solution. The heating device was then turned off (total heating time of about 10 minutes). The solution was allowed to stand for over two hours to allow the solution to slowly reach room temperature, at which point the solution was white and cloudy. The solution was then chilled at 4° C. After about 7 days, large crystals were observed. The crystals were then isolated and dried.

Figure 5:
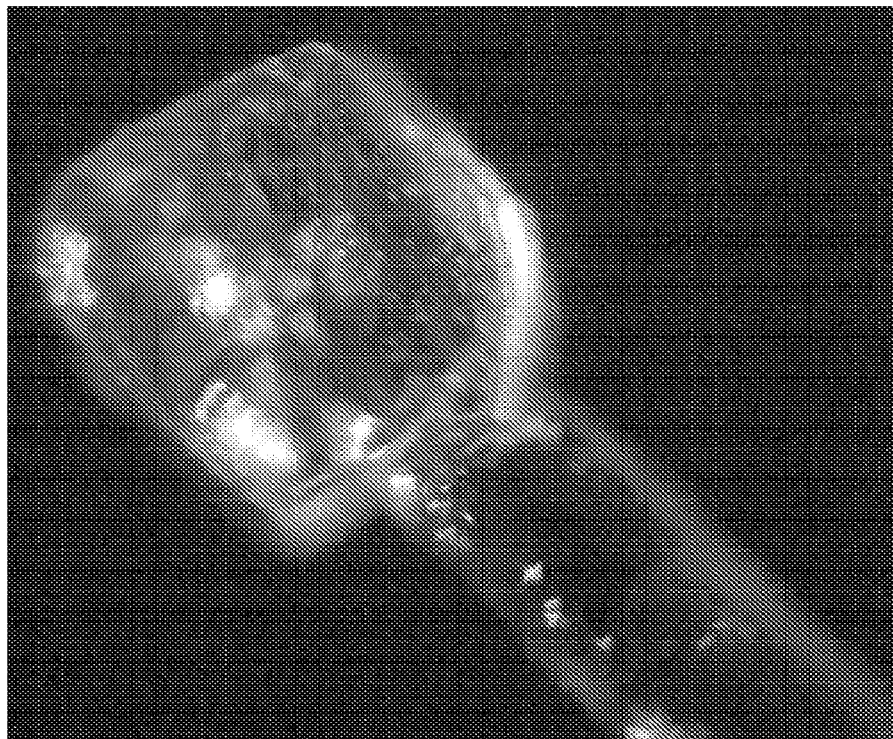
FIG. 5 is a microscopic image of a unit cell crystal.

The crystal structure was determined with a single crystal X-ray Diffractometer (Nonius Kappa-CCD Diffractometer equipped with Oxford Cryostream Liquid Nitrogen Cooler using MoKα radiation). The size of the chunk crystal was 0.45×0.25×0.20 mm. A large crystal was cut along the crystallographic dimension to obtain appropriate crystal size for analysis (FIG. 5). Data was collected at a temperature of 294° K and 120° K.

The crystal exhibited a monoclinic symmetry ($P2_1/C$ space group), with the following unit-cell parameters:
Axis (Å): a=11.631, b=7.057, c=42.532
Angle (°): B=104.595, A=C=90
V (Å$^3$): 3378.4
Calculated density (g/cm$^3$): 1.430
Reflection #: 20143

The crystals were found to consist of the 4-[2-(2,4,6-trifluorophenoxymethyl)-phenyl]piperidine cation, chloride anion and water molecules. In each unit cell, there were 2.56 water molecules associated with eight drug molecule pairs (eight 4-[2-(2,4,6-trifluorophenoxymethyl)phenyl]piperidine cations and eight chloride anions), i.e., there was approximately one water molecule per each three drug molecule pairs, where each drug molecule pair consisted of: one 4-[2-(2,4,6-trifluorophenoxymethyl)phenyl]piperidine cation and one chloride anion. Thus, in one embodiment of the invention, about 0.32 moles of water are present for every one mole of the 4-[2-(2,4,6-trifluorophenoxymethyl)-phenyl]piperidine hydrochloride salt; the formula for such a crystal can be written as: 1 4-[2-(2,4,6-trifluorophenoxymethyl)phenyl]piperidine. 1 HCl. 0.32 $H_2O$.

The crystal is built around the water molecule and the water content was determined from the water occupancy factor in the unit cell. The water occupancy factor was calculated using the thermal motion parameters of the atoms and overall observed structure factors.

Assay 1 hSERT, hNET, and hDAT Binding Assays

Membrane radioligand binding assays were used to measure competitive inhibition of labeled ligand ($^3$H-citalopram or $^3$H-nisoxetine or $^3$H-WIN35428) binding to membranes prepared from cells expressing the respective human recombinant transporter (hSERT or hNET or hDAT) in order to determine the $pK_i$ values of test compounds at the transporters.

Membrane Preparation from Cells Expressing hSERT, hNET, or hDAT

Recombinant human embryonic kidney (HEK-293) derived cell lines stably transfected with hSERT or hNET, respectively, were grown in DMEM medium supplemented with 10% dialyzed FBS (for hSERT) or FBS (for hNET), 100 μg/ml penicillin, 100 μg/ml streptomycin, 2 mM L-glutamine and 250 μg/ml of the aminoglycoside antibiotic G418, in a 5% $CO_2$ humidified incubator at 37° C. When cultures reached 80% confluence, the cells were washed thoroughly in PBS (without $Ca^{2+}$ and $Mg^{2+}$) and lifted with 5 mM EDTA in PBS. Cells were pelleted by centrifugation, resuspended in lysis buffer (10 mM Tris-HCl, pH7.5 containing 1 mM EDTA), homogenized, pelleted by centrifugation, then resuspended in 50 mM Tris-HCl, pH 7.5 and 10% sucrose at 4° C. Protein concentration of the membrane suspension was determined using a Bio-Rad Bradford Protein Assay kit. Membranes were snap frozen and stored at −80° C. Chinese hamster ovary membranes expressing hDAT (CHO-DAT) were purchased from PerkinElmer and stored at −80° C.

Binding Assays

Binding assays were performed in a 96-well assay plate in a total volume of 200 μl assay buffer (50 mM Tris-HCl, 120 mM NaCl, 5 mM KCl, pH 7.4) with 0.5, 1, and 3 μg membrane protein, for SERT, NET and DAT, respectively. Saturation binding studies, to determine radioligand $K_d$ values for $^3$H-citalopram, $^3$H-nisoxetine, or $^3$H-WIN35428, respectively were conducted using 12 different radioligand concentrations ranging from 0.005-10 nM ($^3$H-citalopram); 0.01-20 nM ($^3$H-nisoxetine) and 0.2-50 nM ($^3$H-WIN35428). Displacement assays for determination of $pK_i$ values of test compounds were conducted with 1.0 nM $^3$H-citalopram, 1.0 nM $^3$H-nisoxetine or 3.0 nM $^3$H-WIN35428, at 11 different concentrations of test compound ranging from 10 pM to 100 μM.

Stock solutions (10 mM in DMSO) of test compound were prepared and serial dilutions made using Dilution Buffer (50 mM Tris-HCl, 120 mM NaCl, 5 mM KCl, pH 7.4, 0.1% BSA, 400 μM ascorbic acid). Non-specific radioligand binding was determined in the presence of 1 μM duloxetine, 1 μM desipramine or 10 μM GBR12909 (each in Dilution Buffer) for the hSERT, hNET or hDAT assays, respectively.

Following a 60 minute incubation at 22° C. (or a period sufficient to reach equilibrium), the membranes were harvested by rapid filtration over a 96-well UniFilter GF/B plate, pretreated with 0.3% polyethyleneimine, and washed 6 times with 300 μl wash buffer (50 mM Tris-HCl, 0.9% NaCl, pH 7.5 at 4° C.). Plates were dried overnight at room temperature, ~45 μl of MicroScint™-20 (Perkin Elmer) added and bound radioactivity quantitated via liquid scintillation spectroscopy. Competitive inhibition curves and saturation isotherms were analyzed using GraphPad Prism Software package (GraphPad Software, Inc., San Diego, Calif.). $IC_{50}$ values were generated from concentration response curves using the Sigmoidal Dose Response (variable slope) algorithm in Prism GraphPad. $K_d$ and $B_{max}$ values for the radioligand were generated from saturation isotherms using the Saturation Binding Global Fit algorithm in Prism GraphPad. $pK_i$ (negative decadic logarithm of $K_i$) values for test compounds were calculated from the best-fit $IC_{50}$ values, and the $K_d$ value of the radioligand, using the Cheng-Prusoff equation (Cheng & Prusoff (1973) *Biochem. Pharmacol.* 22(23):3099-3108): $K_i=IC_{50}/(1+[L]/K_d)$, where [L]=concentration radioligand.

The compound of Example 1 (TFA salt) was tested in this assay and found to exhibit a SERT $pK_i \geq 7.9$ and a NET $pK_i \geq 8.0$.

Assay 2 hSERT, hNET, and hDAT Neurotransmitter Uptake Assays

Neurotransmitter uptake assays were used to measure competitive inhibition of $^3$H-serotonin ($^3$H-5-HT), $^3$H-norepinephrine ($^3$H-NE), and $^3$H-dopamine ($^3$H-DA) uptake into cells expressing the respective transporter (hSERT, hNET or hDAT) in order to determine the $pIC_{50}$ values of test compounds at the transporters.

$^3$H-5-HT, $^3$H-NE, and $^3$H-DA Uptake Assays

HEK-293 derived cell lines stably-transfected with hSERT, hNET, or hDAT, respectively, were grown in DMEM medium supplemented with 10% dialyzed FBS (for hSERT) or FBS (for hNET and hDAT), 100 μg/ml penicillin, 100 μg/ml streptomycin, 2 mM L-glutamine and 250 μg/ml of the aminoglycoside antibiotic G418 (for hSERT and hNET) or 800 ug/ml (for hDAT), in a 5% $CO_2$ humidified incubator at 37° C. When cultures reached 80% confluence, the cells were washed thoroughly in PBS (without $Ca^{2+}$ and $Mg^{2+}$) and lifted with 5 mM EDTA in PBS. Cells were harvested by centrifugation at 1100 rpm for 5 minutes, washed once by resuspension in PBS, then centrifuged. The supernatant was discarded and the cell pellet resuspended, by gentle trituration, in room temperature Krebs-Ringer bicarbonate buffer containing HEPES (10 mM), $CaCl_2$ (2.2 mM), ascorbic acid (200 μM) and pargyline (200 μM), pH 7.4. The final concentration of cells in the cell suspension was $7.5 \times 10^4$ cells/ml, $1.25 \times 10^5$ cells/ml, and $5.0 \times 10^4$ cells/ml for SERT, NET, and DAT cell lines, respectively.

Neurotransmitter uptake assays were performed in a 96-well assay plate in a total volume of 400 μL assay buffer (Krebs-Ringer bicarbonate buffer containing HEPES (10 mM), $CaCl_2$ (2.2 mM), ascorbic acid (200 μM) and pargyline (200 μM), pH 7.4) with $1.5 \times 10^4$ and $2.5 \times 10^4$ cells, for SERT and NET, respectively. Competition assays for determination of $pIC_{50}$ values of test compounds were conducted with 11 different concentrations, ranging from 10 pM to 100 μM. Stock solutions (10 mM in DMSO) of test compound were prepared and serial dilutions prepared using 50 mM Tris-HCl, 120 mM NaCl, 5 mM KCl, pH 7.4, 0.1% BSA, 400 μM ascorbic acid. Test compounds were incubated for 30 minutes at 37° C. with the respective cells, prior to addition of radiolabeled neurotransmitter, $^3$H-5-HT (20 nM final concentration), $^3$H-NE (50 nM final concentration), or $^3$H-DA (100 nM final concentration). Non-specific neurotransmitter uptake was determined in the presence of 2.5 μM duloxetine or 2.5 μM desipramine (each in Dilution Buffer) for the hSERT, hNET, or hDAT assays, respectively.

Following a 10 minute incubation, at 37° C., with radioligand, the cells were harvested by rapid filtration over a 96-well UniFilter GF/B plate, pretreated with 1% BSA, and washed 6 times with 650 μl wash buffer (ice cold PBS). Plates were dried overnight at 37° C., ~45 μl of MicroScint™-20 (Perkin Elmer) added and incorporated radioactivity quantitated via liquid scintillation spectroscopy. Competitive inhibition curves were analyzed using GraphPad Prism Software package (GraphPad Software, Inc., San Diego, Calif.). $IC_{50}$ values were generated from concentration response curves using the Sigmoidal Dose Response (variable slope) algorithm in Prism GraphPad.

Assay 3

Ex Vivo SERT and NET Transporter Occupancy Studies

Ex vivo radioligand binding and neurotransmitter uptake assays were used to determine the in vivo occupancy of SERT and NET, in selected brain regions, following in vivo administration (acute or chronic) of test compounds. Following administration of test compound (by intravenous, intraperitoneal, oral, subcutaneous or other route) at the appropriate dose (0.0001 to 100 mg/kg), rats (≥n=4 per group) were euthanized at specific time points (10 minutes to 48 hours) by decapitation and the brain dissected on ice. Relevant brain regions were dissected, frozen and stored at −80° C. until use.

Ex Vivo SERT and NET Radioligand Binding Assays

For ex vivo radioligand binding assays, the initial rates of association of SERT ($^3$H-citalopram), and NET-($^3$H-nisoxetine) selective radioligands with rat brain crude homogenates, prepared from vehicle and test compound-treated animals, were monitored (see Hess et al. (2004) *J. Pharmacol. Exp. Ther.* 310(2):488-497). Crude brain tissue homogenates were prepared by homogenizing frozen tissue pieces in 0.15 mL (per mg wet weight) of 50 mM Tris-HCl, 120 mM NaCl, 5 mM KCl, pH 7.4 buffer. Radioligand association assays were performed in a 96-well assay plate in a total volume of 200 μl assay buffer (50 mM Tris-HCl, 120 mM NaCl, 5 mM KCl, 0.025% BSA, pH 7.4) with 650 μg wet weight tissue (equivalent to 25 μg protein). Homogenates were incubated for up to 5 minutes with $^3$H-citalopram (3 nM) and $^3$H-nisoxetine (5 nM), respectively, prior to termination of the assay by rapid filtration over a 96-well UniFilter GF/B plate, pretreated with 0.3% polyethyleneimine. Filters then were washed 6 times with 300 μl wash buffer (50 mM Tris-HCl, 0.9% NaCl, pH 7.4 at 4° C.). Non-specific radioligand binding was determined in the presence of 1 μM duloxetine, or 1 μM despiramine, for $^3$H-citalopram or $^3$H-nisoxetine, respectively. The plates were dried overnight at room temperature, ~45 μl of MicroScint™-20 (Perkin Elmer) added and bound radioactivity quantitated via liquid scintillation spectroscopy. The initial rates of association of $^3$H-citalopram and $^3$H-nisoxetine were determined by linear regression using GraphPad Prism Software package (GraphPad Software, Inc., San Diego, Calif.). The average rate of radioligand association to brain tissue homogenates from vehicle-treated animals was determined. The % occupancy of test compounds then was determined using the following equation:

% occupancy=100×(1−(initial rate association for test compound-treated tissue/mean rate association for vehicle-treated tissue))

$ED_{50}$ values were determined by plotting the log 10 of the dose of the test compound against the % occupancy. $ED_{50}$ values were generated from concentration response curves using the Sigmoidal Dose Response (variable slope) algorithm in GraphPad Prism.

Ex Vivo SERT and NET Uptake Assays

Ex vivo neurotransmitter uptake assays, in which the uptake of $^3$H-5-HT or $^3$H-NE into rat brain crude homogenates, prepared from vehicle and test compound-treated animals, were used to measure in vivo SERT and NET transporter occupancy (see Wong et al. (1993) *Neuropsychopharmacology* 8(1):23-33). Crude brain tissue homogenates were prepared by homogenizing frozen tissue pieces in 0.5 mL (per mg wet weight) of 10 mM HEPES buffer pH 7.4, containing 0.32 M sucrose, 200 μM ascorbic acid and 200 μM pargyline, at 22° C. Neurotransmitter uptake assays were performed in a 96-well Axygen plate in a total volume of 350 μl assay buffer (Krebs-Ringer bicarbonate buffer with 10 mM HEPES, 2.2 mM $CaCl_2$, 200 μM ascorbic acid and 200 μM pargyline, pH 7.4) with 50 μg protein. Homogenates were incubated for 5 minutes at 37° C. with $^3$H-5-HT (20 nM) and $^3$H-NE (50 nM), respectively, prior to termination of the assay by rapid filtration over a 96-well UniFilter GF/B plate, pretreated with 1% BSA. Plates were washed 6 times with 650 μl wash buffer (ice cold PBS) and dried overnight at 37° C., prior to addition of ~45 μl of MicroScint™-20 (Perkin Elmer) added. Incorporated radioactivity was quantitated via liquid scintillation spectroscopy. Non-specific neurotransmitter uptake was determined in parallel assays in which tissue homogenates were incubated with $^3$H-5-HT (20 nM) or $^3$H-NE (50 nM) for 5 minutes at 4° C.

Assay 4

Other Assays

Other assays that were used to evaluate the pharmacological properties of test compounds include, but are not limited to, cold ligand binding kinetics assays (Motulsky and Mahan (1984) *Molecular Pharmacol.* 25(1): 1-9) with membranes prepared from cells expressing hSERT or hNET;

conventional membrane radioligand binding assays using radiolabeled, for example, tritiated, test compound; radioligand binding assays using native tissue from, for example rodent or human brain; neurotransmitter uptake assays using human or rodent platelets; neurotransmitter uptake assays using crude, or pure, synaptosome preparations from rodent brain.

Assay 5

Formalin Paw Test

Compounds are assessed for their ability to inhibit the behavioral response evoked by a 50 μl injection of formalin (5%). A metal band is affixed to the left hind paw of male Sprague-Dawley rats (200-250 g) and each rat is conditioned to the band for 60 minutes within a plastic cylinder (15 cm diameter). Compounds are prepared in pharmaceutically acceptable vehicles and administered systemically (i.p., p.o.) at pre-designated times before formalin challenge. Spontaneous nociceptive behaviors consisting of flinching of the injected (banded) hind paw are counted continuously for 60 minutes using an automated nociception analyzer (UCSD Anesthesiology Research, San Diego, Calif.). Antinociceptive properties of test articles are determined by comparing the number of flinches in the vehicle and compound-treated rats (Yaksh et al., "An automated flinch detecting system for use in the formalin nociceptive bioassay" (2001) *J. Appl. Physiol.* 90(6):2386-2402).

Assay 6

Spinal Nerve Ligation Model

Compounds are assessed for their ability to reverse tactile allodynia (increased sensitivity to an innocuous mechanical stimulus) induced by nerve injury. Male Sprague-Dawley rats are surgically prepared as described in Kim and Chung "An experimental model for peripheral neuropathy produced by segmental spinal nerve ligation in the rat" (1992) *Pain* 50(3):355-363. Mechanical sensitivity is determined as the 50% withdrawal response to innocuous mechanical stimuli (Chaplan et al., "Quantitative assessment of tactile allodynia in the rat paw" (1994) *J. Neurosci. Methods* 53(1):55-63) before and after nerve injury. One to four weeks post-surgery, compounds are prepared in pharmaceutically acceptable vehicles and administered systemically (i.p., p.o.). The degree of nerve injury-induced mechanical sensitivity before and after treatment serves as an index of the compounds' antinociceptive properties.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A solid pharmaceutically composition comprising:
   (a) a crystalline hydrochloride salt of 4-[2-(2,4,6-trifluorophenoxymethyl)-phenyl]piperidine characterized by (a) a powder x-ray diffraction pattern comprising diffraction peaks at 2θ values of 4.44±0.20, 10.22±0.20, 16.06±0.20, 21.78±0.20, 23.76±0.20, 26.32±0.20, 27.24±0.20, 29.60±0.20, and 31.94±0.20; or (b) a differential scanning calorimetry trace which has a melting point of about 196.9° C.; and
   (b) a pharmaceutically acceptable carrier selected from starch, microcrystalline cellulose, lactose, sucrose, glucose, mannitol, silicic acid and mixtures thereof.

2. The pharmaceutical composition of claim 1, wherein the crystalline hydrochloride salt of 4-[2-(2,4,6-trifluorophenoxymethyl)phenyl]piperidine is characterized by a powder x-ray diffraction pattern comprising diffraction peaks at 2θ values of 4.44±0.20, 10.22±0.20, 16.06±0.20, 21.78±0.20, 23.76±0.20, 26.32±0.20, 27.24±0.20, 29.60±0.20, and 31.94±0.20.

3. The pharmaceutical composition of claim 1, wherein the crystalline hydrochloride salt of 4-[2-(2,4,6-trifluorophenoxymethyl)phenyl]piperidine is characterized by a differential scanning calorimetry trace which has a melting point of about 196.9° C.

4. The pharmaceutical composition of claim 1, wherein the pharmaceutically acceptable carrier is microcrystalline cellulose.

5. The pharmaceutical composition of claim 1, wherein the pharmaceutically acceptable carrier is lactose.

6. The pharmaceutical composition of claim 1, wherein the pharmaceutical composition further comprises a lubricant selected from talc, calcium stearate, magnesium stearate, solid polyethylene glycol, sodium lauryl sulfate and mixtures thereof.

7. The pharmaceutical composition of claim 6, wherein the lubricant is magnesium stearate.

8. The pharmaceutical composition of claim 1, wherein the pharmaceutical composition contains about 1 milligram to about 20 milligrams of the crystalline hydrochloride salt of 4-[2-(2,4,6-trifluorophenoxymethyl)phenyl]piperidine.

9. The pharmaceutical composition of claim 1, wherein the pharmaceutical composition contains about 1 milligram to about 15 milligrams of the crystalline hydrochloride salt of 4-[2-(2,4,6-trifluorophenoxymethyl)phenyl]piperidine.

10. The pharmaceutical composition of claim 1, wherein the pharmaceutical composition contains about 1 milligram to about 10 milligrams of the crystalline hydrochloride salt of 4-[2-(2,4,6-trifluorophenoxymethyl)phenyl]piperidine.

11. The pharmaceutical composition of claim 1, wherein the pharmaceutical composition contains about 10 milligrams of the crystalline hydrochloride salt of 4-[2-(2,4,6-trifluorophenoxymethyl)phenyl]piperidine.

* * * * *